(12) United States Patent
Boussemart et al.

(10) Patent No.: US 7,707,927 B2
(45) Date of Patent: May 4, 2010

(54) BEVERAGE MACHINE WITH HEIGHT-ADJUSTABLE DEVICE FOR CONTROLLING DISTANCE BETWEEN BEVERAGE RECIPIENT AND OUTLET

(75) Inventors: Christophe S. Boussemart, Lugrin (FR); Fabien Ludovic Agon, Le Bouveret (CH); Antoine Ryser, Lausanne (CH)

(73) Assignee: Nestec S.A., Vevey (CH)

( * ) Notice: Subject to any disclaimer, the term of this patent is extended or adjusted under 35 U.S.C. 154(b) by 365 days.

(21) Appl. No.: 11/745,234

(22) Filed: May 7, 2007

(65) Prior Publication Data

US 2007/0209521 A1 Sep. 13, 2007

Related U.S. Application Data

(63) Continuation of application No. PCT/EP2005/009693, filed on Sep. 9, 2005.

(30) Foreign Application Priority Data

Nov. 11, 2004 (EP) .................................. 04026844

(51) Int. Cl.
*A47J 31/00* (2006.01)
(52) U.S. Cl. .......................................... 99/280; 99/275
(58) Field of Classification Search ........... 99/279–323, 99/275–277, 495, 452–455; 222/190, 129.1, 222/145.5; 426/433–435, 594, 595, 112, 426/144
See application file for complete search history.

(56) References Cited

U.S. PATENT DOCUMENTS

| | | | |
|---|---|---|---|
| 2,836,300 A | | 5/1958 | Serr .......................... 210/248 |
| 5,402,707 A | | 4/1995 | Fond et al. .................... 99/295 |
| 5,603,254 A | * | 2/1997 | Fond et al. .................... 99/295 |
| 5,649,472 A | * | 7/1997 | Fond et al. .................... 99/295 |
| 5,656,316 A | * | 8/1997 | Fond et al. .................. 426/433 |
| 5,762,987 A | | 6/1998 | Fond et al. .................. 426/433 |
| 5,826,492 A | * | 10/1998 | Fond et al. .................... 99/295 |
| 5,895,672 A | * | 4/1999 | Cooper ........................ 426/79 |

(Continued)

FOREIGN PATENT DOCUMENTS

CA 2 260 352 A1 7/2000

(Continued)

OTHER PUBLICATIONS

European Search Report dated Jul. 1, 2005 from application No. EP 04026844.3.

(Continued)

*Primary Examiner*—Timothy F. Simone
(74) *Attorney, Agent, or Firm*—Winston & Strawn LLP

(57) ABSTRACT

A beverage machine having a height-adjustment device that includes a movable support plate for adjusting the position of the recipient relative to at least one beverage outlet. The support plate is movable relative to the at least one beverage outlet. The machine also includes a displacement mechanism for displacing the support plate relative to the outlet. The displacement mechanism includes a motorized driver for driving the displacement mechanism, a controller for controlling the actuation of the driver and which is configured to set a predetermined distance between the outlet and the recipient. A drip-collecting device can also be selectively provided to collect liquid falling from the beverage outlet when the recipient is not present.

23 Claims, 10 Drawing Sheets

U.S. PATENT DOCUMENTS

| | | | | |
|---|---|---|---|---|
| 5,897,899 A | * | 4/1999 | Fond | 426/112 |
| 5,931,080 A | | 8/1999 | Boada | 99/293 |
| 6,068,871 A | * | 5/2000 | Fond et al. | 426/433 |
| 6,725,762 B2 | * | 4/2004 | Kollep et al. | 99/283 |
| 6,758,130 B2 | * | 7/2004 | Sargent et al. | 99/295 |
| 6,810,795 B1 | * | 11/2004 | Hsu | 99/453 |
| 7,258,062 B2 | * | 8/2007 | Green | 99/323.1 |
| 2003/0232115 A1 | | 12/2003 | Eckenhausen et al. | 426/477 |
| 2006/0108023 A1 | | 5/2006 | Greiwe et al. | 141/369 |
| 2007/0031558 A1 | | 2/2007 | Lussi | 426/520 |

FOREIGN PATENT DOCUMENTS

| | | |
|---|---|---|
| DE | 202 05 626 U1 | 8/2002 |
| DE | 102 39 595 A1 | 3/2004 |
| EP | 0 585 607 B1 | 3/1994 |
| EP | 0 512 470 B1 | 4/1996 |
| EP | 0 791 321 A1 | 8/1997 |
| EP | 0 604 615 B1 | 9/1998 |
| EP | 1 374 748 A2 | 1/2004 |
| EP | 0 870 457 B1 | 2/2004 |
| EP | 1 472 963 A1 | 11/2004 |
| FR | 2 439 042 | 5/1980 |
| WO | WO 2004/052159 A1 | 6/2004 |

OTHER PUBLICATIONS

International Search Report dated Dec. 22, 2006 from application No. PCT/EP2005/011866.

* cited by examiner

US 7,707,927 B2

BEVERAGE MACHINE WITH HEIGHT-ADJUSTABLE DEVICE FOR CONTROLLING DISTANCE BETWEEN BEVERAGE RECIPIENT AND OUTLET

CROSS-REFERENCE TO RELATED APPLICATIONS

This application is a continuation of International application PCT/EP2005/009693 filed Sep. 9, 2005, the entire content of which is expressly incorporated herein by reference thereto.

BACKGROUND

The present invention generally relates to the field of beverage dispensing machines, in particular, machines that can brew or extract coffee and coffee specialties such as cappuccino and the like or tea.

There is trend to propose beverage machines that are versatile enough to be able to deliver various coffee beverages such as espresso type coffee or coffee specialties such as cappuccino (coffee with a milk froth) or latte (coffee with liquid milk). Typically, those coffee beverages are received in beverage recipients, e.g., cups or glasses, of variable volume. For instance, an espresso coffee or ristretto is served in a small cup of about 40 mL, whereas a cappuccino can be served in a larger/taller cup or glass of from 110 mL to 250 mL. A long black coffee cup can also be served in a 110-mL cup. For cold coffee drinks, one also uses tall glasses.

The coffee beverages must also meet different quality attributes which are important. For instance, an espresso coffee must have a fine and stiff "crema" which is a stable emulsion formed by the oily compounds during extraction of the coffee product in the machine. The extraction process can be finely controlled to provide this crema, when the product is extracted from closed capsules, such as in the processes described in European patent applications 512,470, 604,615 and 870,457 and their US counterparts, U.S. Pat. Nos. 5,402,707, 5,649,472, 5,762,987 and 5,826,492.

With other coffee specialties, one may need to distribute a milk froth on top of the beverage such as with cappuccino-type beverages.

One problem is that due to the variable volumes of recipients for receiving the varied coffee beverages, the distance between the beverage outlet(s) and the recipient cannot be precisely guaranteed. In order for the machine to accommodate different size recipients, the distance between the outlet and the recipient is usually too high. Too high of a distance creates splashing issues.

Surprisingly, it has been found that an incorrect distance can also be detrimental to the quality of the "crema" or foam. For instance, if the distance between the coffee outlet and the recipient is too high, larger bubbles are formed in the coffee "crema". Larger bubbles induce a "crema" which is less stable and less stiff. Therefore, there is a need for controlling and precisely adjusting the distance between the outlet and the recipient as a function of the recipient used in order to solve these hygiene and crema/foam quality problems.

There have been attempts for machines that have height-adjustable discharge outlets. For instance, in WO 2004/052159, the beverage outlet is borne by a height-adjustable slider. Therefore, A full beverage delivery block must be made moveable relative to stationary cups underneath. It is uneasy to make the beverage delivery moveable to an extent that encompasses a wide range of cup sizes. In particular, this complicates the construction of the machine when the machine comprises an extraction module for closed capsules because the module requires to be precisely closed about the capsule in a repetitive manner. The module must also be linked to a hot water line that needs to stand the repetitive height changes of the module. Furthermore, there is no indication how precise the height adjustment can be controlled in WO 2004/052159, which is also a problem because only containers of standardized shapes can so be used otherwise the quality of the beverage's foam cannot be guaranteed.

European patent application EP 0 585 607 relates to an espresso machine which comprises a support plate for the recipient that can be adjusted in height. The plate is supported on an appliance base with a collecting tray arranged therebetween which receives the surplus liquid and is detachably connected with the collecting tray. First of all, the adjustment of the support plate is merely mechanical and carried out by the user himself. Therefore, it cannot be controlled with all the precision and knowledge required. Secondly, the drip tray assembly raises hygienic problems because splashing is likely to occur on the support plate; and because the distance between the support plate and the drip tray increases for short cups of coffee, the liquid projections and dripping may not be well collected in the drip tray and the service area is likely to require frequent cleaning.

Therefore, there is a need for a beverage machine that can deliver a foamy beverage or beverage with "crema" with optimized foam/crema quality. There is also a need for a beverage machine that can deliver beverages from various recipient sizes without splashing issues. The present invention now satisfies these needs.

SUMMARY OF THE INVENTION

The present invention relates to a beverage machine having a height-adjustment mechanism for the position of the beverage recipient relative to the beverage outlet, that can be precisely and automatically controlled and requires as less intervention from the user as possible. Additionally, this height-adjustment mechanism requires less cleaning than conventional machines.

According to a first aspect of the invention, the beverage machine for the preparation of beverages such as espresso coffee and coffee specialties comprises a height adjustment device comprising a movable support plate for adjusting the position of the recipient relative to at least one beverage outlet when resting on a support plate, wherein the support plate is movable relative to the at least one beverage outlet and comprises a displacement mechanism for displacing the support plate relative to the outlet.

The height adjustment device comprises a motorized driver for driving the displacement mechanism and a controller for controlling the actuation of the driver which are configured to control the distance between the outlet and the recipient as a function of the size of the recipient being placed on the support plate.

According to one feature, the controller controls the distance as a function of at least one height related dimension of the recipient being placed on the support plate. As a result, the optimal distance can be determined at each beverage delivery cycle.

According to another feature, the a controller comprises at least one sensor that detects the position of at least one part of the recipient being placed on the support plate and a control unit that stops the motorized driver in response to the sensor's input to the control unit. For instance, the sensor can be advantageously positioned in a predetermined position below the beverage outlet to detect the position of the upper edge of the recipient.

According to a second aspect, the invention relates to a beverage machine for the preparation of beverages wherein the machine comprising a frame, a beverage outlet adapted to deliver a beverage in a recipient placed in a support plate of a beverage service area, a drip collecting device which is configured to be selectively placed above the beverage recipient and below or around the beverage outlet to collect liquid or froth when the machine is not delivering the beverage or when the recipient is removed from the beverage service area. The motorized driver can comprise a drive electrical motor and a continuous displacement transmission system that is arranged to be driven by the electrical motor to move the support plate in a continuous manner.

This second aspect of the invention provides a clean and lower cost solution for removing the inconvenience of dripping of liquid after the recipient has been removed from the service area. It simplifies the beverage service area and provides a simpler service area of controllable height to adjust the beverage delivery distance according to the size of the recipient. For instance, the support plate can thus be omitted and the beverage recipient can directly stand on an external support (e.g., a kitchen table). In an alternative, a simple support plate can be provided that can be adjusted in height but does not need to carry a bulky drip tray with the risk that liquid could flow over the tray when it is moved up and down.

According to another feature of the invention, the drip collecting device is movable between a collecting position in which it is placed beneath the outlet and a retracted position in which it is placed away from the outlet.

The invention also relates to a method for the preparation of a beverage in a beverage machine comprising a beverage preparation head and a beverage outlet and a service area for positioning of the recipient. The method comprises selectively placing a drip-collecting device in the service area to collect liquid falling from the beverage outlet before the liquid can reach the service area.

BRIEF DESCRIPTION OF THE DRAWING FIGURES

Further advantages, objects and features of the present invention will appear when reading the following detailed explanation of an embodiment of the present invention taken in conjunction with the appended drawing figures, wherein:

FIG. 1 shows a perspective frontal view of a device according to the present invention, FIG. 2 shows a perspective rear view of the device of FIG. 1, FIG. 3 shows a perspective frontal view of a detail of the invention, in particular, of the drip collector system in a retracted position, FIG. 4 shows the front view of FIG. 3, FIG. 5 shows a perspective view similar to FIG. 3 but in a deployed collecting position of the drip collector system, FIG. 6 shows the front view of FIG. 5, FIG. 7 shows schematically a control unit of the present invention;

DETAILED DESCRIPTION OF THE PREFERRED EMBODIMENTS

U.S. patent application Ser. No. 11/743,975 filed May 3, 2007 discloses certain features of devices that are utilizable in the present invention and for that reason the entire content of that patent application is expressly incorporated herein by reference thereto.

Figure 1:
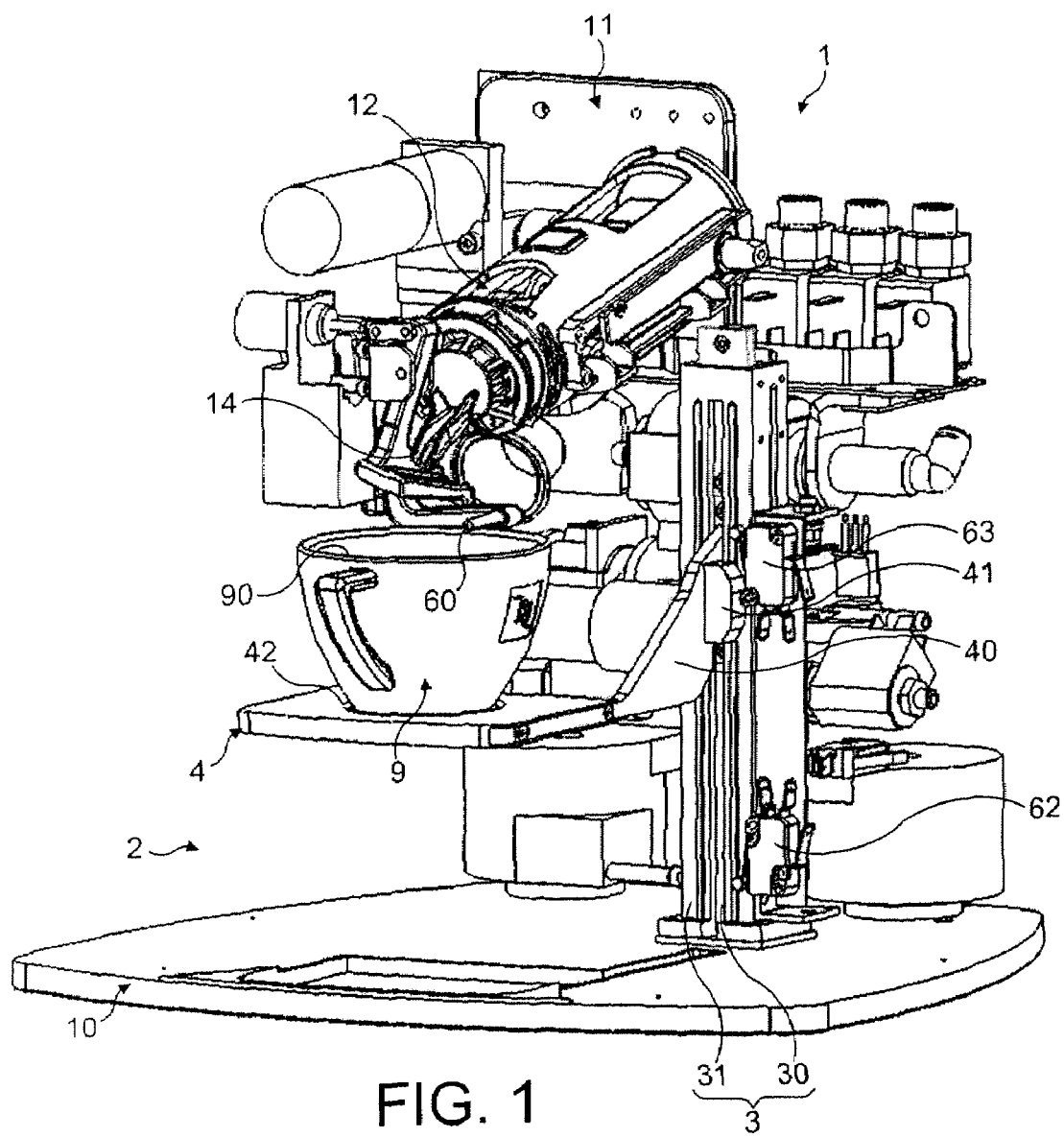

A detailed embodiment of the present invention will be explained. FIG. 1 shows a coffee machine 1 with its cover being removed for showing a frame 10 onto which is assembled the main parts of the system.

The frame 10 comprises an extraction module 11 positioned in the upper portion of the machine. The module 11 is such that it can extract capsules after the capsule is inserted through a complementary shaped slot 12 of the module. The capsule usually contains a beverage product such as a roast and ground coffee, tea or cocoa. The extraction module is fed in hot pressurized water by a water pump 13 such as a piston pump. Water can be heated before reaching the head through a heater 15 such as a thermoblock. The extraction module can comprise tearing or puncturing elements enabling to open the capsule under pressure. As a matter of illustration, a principle of known extraction of closed capsules is described in various documents, such as EP 0512470 B1, while an example of an extraction module is described in International patent application WO 2005/004683. The extraction module generally comprises a front beverage outlet 14 forming a short duct extending forwardly and downwardly from the body of the module.

At the vertical below the beverage outlet 14 is positioned a beverage service area 2 comprising a height adjustment device 3 which is conceived to properly adjust the position of a beverage recipient 9 (e.g., an appropriate beverage container such as a coffee cup, a latte mug, a macchiato glass, etc.) at a relative position with respect to the beverage outlet. The height adjustment device comprises a support plate 4 and a displacement mechanism 5 for displacing the support plate up and down relative to the outlet. The height adjustment device 3 can be associated to a drip collecting device 8 which will be described herein with relation to FIGS. 3 to 6. However, the present invention in view of the adjustment of the distance between the recipient and beverage outlet can be utilized without the drip-collecting device.

The support plate 4 is guided in linear vertical movement through a rectilinear groove 30 performed within a side profiled member 31 of the frame. The support plate can comprise a lateral projection 40 which can fit in the groove to be capable of sliding along the groove. On the side of the lateral projection is positioned a reference protrusion 41 that protrudes outwards to cooperate with the different position sensors as will be explained later on. The support plate 4 can also comprise a central recess 42 for positioning a recipient in a more stable manner on the plate.

Figure 2:
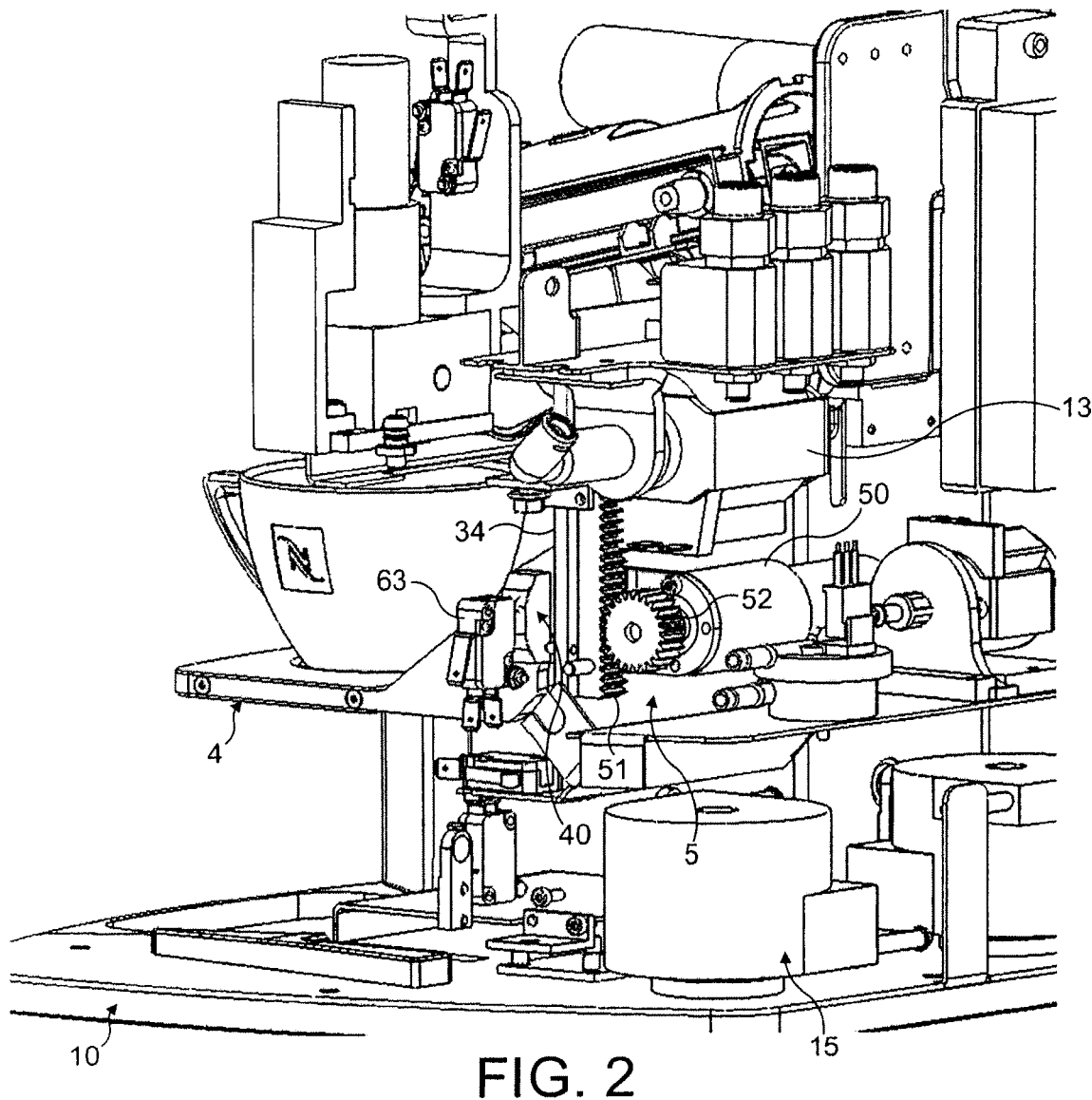
Figure 3:
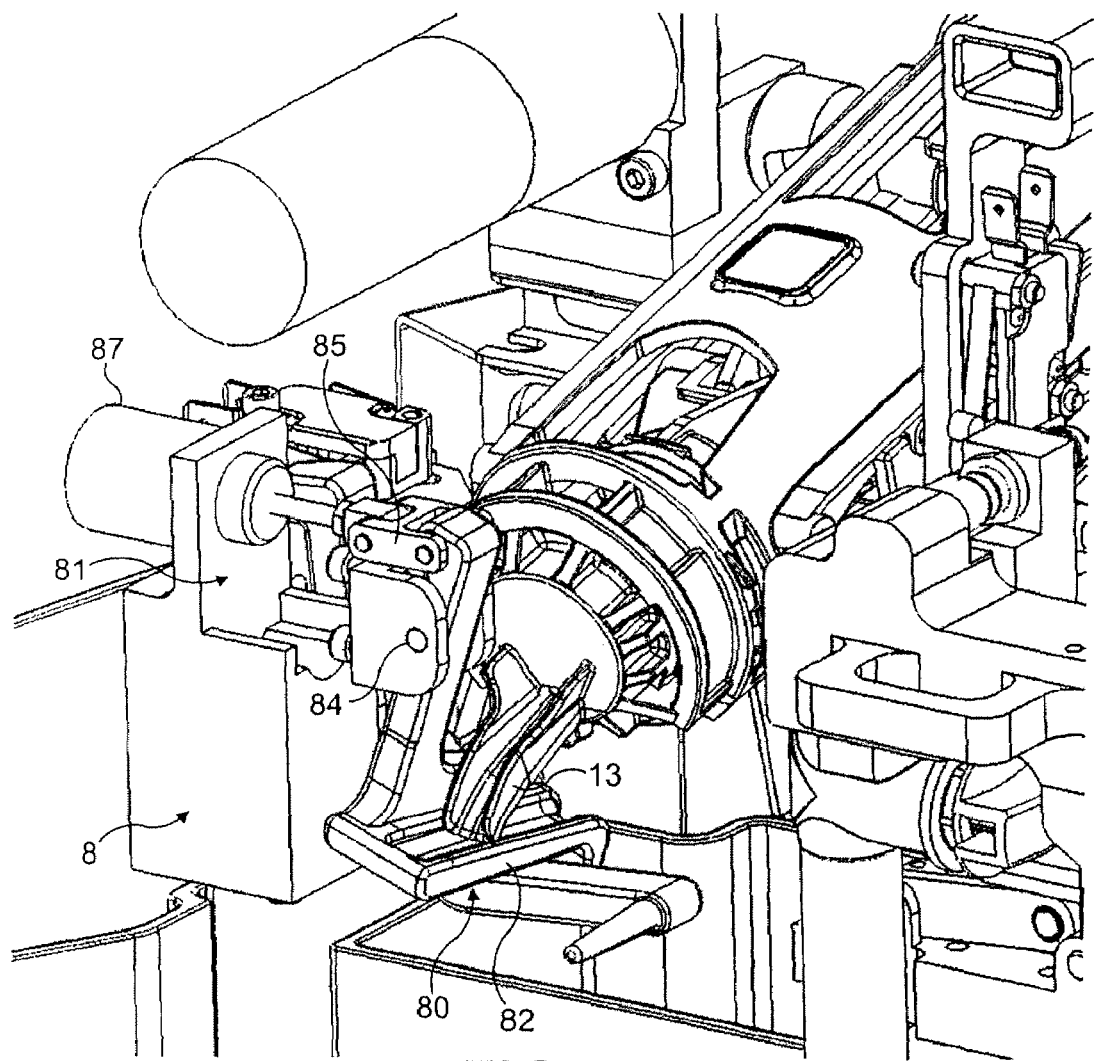

As can be seen from FIG. 2, the displacement mechanism 5 comprises a continuous displacement system that is arranged to be driven by a motor 50 that can move the support plate 4 up and down in a continuous manner. For this, a gear rack 51 is attached to the lateral projection 40 at the other side of the profiled member 31. The gear rack is vertically arranged and sufficiently long to move the support plate at an amplitude sufficient from the bottom of the service area to near the top of the service area so as to accommodate recipients within a wide range of sizes. The gear rack co acts with a gear wheel 52 attached to the electrical motor 50. Of course, a set of wheels can be provided to offer a suitable speed reduction, if necessary.

Other designs of motorized driver can be envisaged. For example, co-pending U.S. patent application Ser. No. 11/743,975 describes a system utilizing a vertically arranged threaded spindle linked to the drive motor and a complementary threaded ring attached to the support; which ring travels along the rotary spindle 25 in response to the rotation of the motor. The system is preferably continuous in the sense that the support plate can take any possible vertical position in relation to a size of recipient. In other terms, two different heights of recipients should lead to position the support plate in two different vertical positions. It is to be noted that an incremental or stepwise displacement is considered as being continuous if the increment is not larger than about 10 mm.

The invention further comprises a controller that are capable of controlling actuation of the motorized driver in such a manner that the recipient on the support surface can be placed at a controlled distance from the beverage outlet. In particular, the a controller comprises at least one sensing means 60 and a control unit 61 (see FIG. 7). One sensing means is a means that detects the reference position of at least a part of the recipient. Preferably, the part of the recipient which is detected by the sensing means is the upper rim 90 of the recipient as it usually corresponds to the highest point of the recipient and therefore, the closest point to the beverage outlet. A preferred sensing means is an electromechanical or light beam-emitting sensor 60. The sensor 60 is positioned in a fixed predetermined vertical position below the beverage outlet to ensure that the recipients are all and always stopped at a same distance from the beverage outlet whatever the height of the recipients and whatever the distance of the support plate from the beverage outlet. The position of the sensor is determined to provide an optimal distance range for the beverage to be distributed. For instance, for coffee based product, the distance can be preferentially chosen between about 20 to 45 mm. The sensor can be a plate or finger made of relatively flexible or be hinged to prevent breaking in case of defective working of the system. When the cup rim contacts the sensor, an input signal is sent to the control unit. Depending on the location of the sensor 60, the control unit may further command a downward motion of the cup support plate to properly position the cup in its final delivery distance from the beverage outlet.

Position sensing means can be further installed to determine the end positions of the support plate. This proves to be useful to ensure a convenient loading of the support plate with the recipient of whatever size and for ensuring that extraction cannot be started until a recipient is loaded on the movable support plate.

A first position sensor 62 can be placed fixedly on the profile member and close to the bottom of the beverage service area. This position sensor 62 senses when the reciprocating support plate reaches the lowest admitted position. The sensor can be an electromechanical switch which is mechanically actuated by the reference protrusion 41 of the support plate when the plate reaches the low position of reference. One advantage of a low position sensor is that one ensures that the support plate is initialised in a same (low) position before each beverage preparation cycle so that a step for the recipient detection can start at each cycle and all the recipients can be detected of whatever size that fits between the low position and the cup rim sensor level.

A second position sensor 63 is also preferably placed to sense the highest admitted position for the support plate. In a similar way, the sensor can be an electromagnetic switch which is mechanically actuated by the reference protrusion 41 of the support plate when the plate reaches the highest position of reference not to be exceeded by the support plate. The advantage of the high position sensor lies essentially in controlling whether or not a recipient has been properly been placed on the support plate while the beverage machine is ready to deliver a beverage. In the event, the high position sensor is sensed by the support plate, this indicates that no recipient has been detected by the cup rim sensor 90. As a result, the beverage machine can be prevented from delivering the beverage.

Of course, the electromechanical switches could be replaced by other types of sensors, for instance, visual detectors such as light beams.

FIGS. 3 to 6 illustrate another aspect of the beverage machine of the invention. The inventive principle lies in having a drip-collecting device 8 which collects liquid falling from the beverage outlet before the liquid can reach the recipient. The drip-collecting device comprises a liquid collecting device that is movable relative to the beverage outlet.

As "relatively movable", one means that either the collecting device is movable and the beverage outlet is fixed, or the collecting device is fixed and the beverage outlet is movable or, alternatively, both the collecting device and the beverage outlet are movable.

Figure 4:
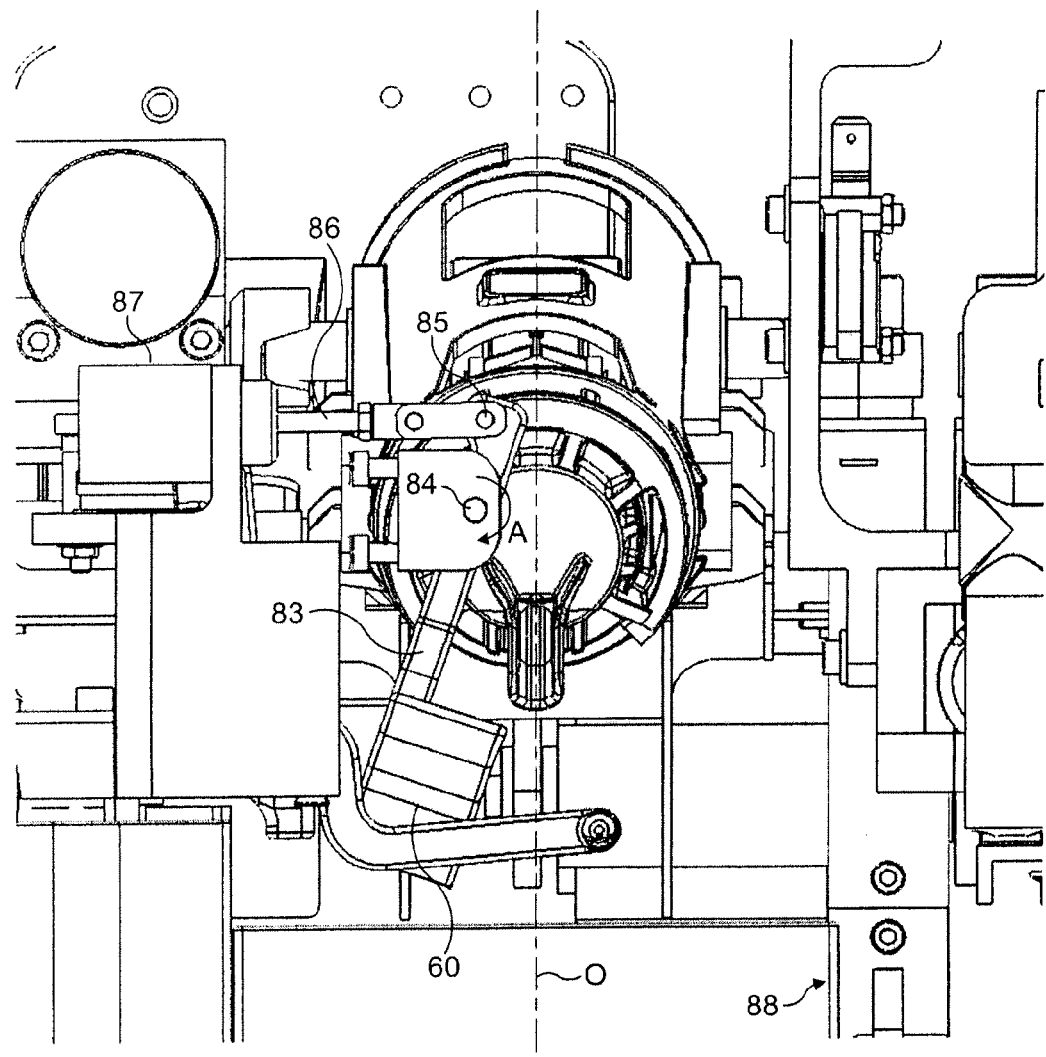
Figure 5:
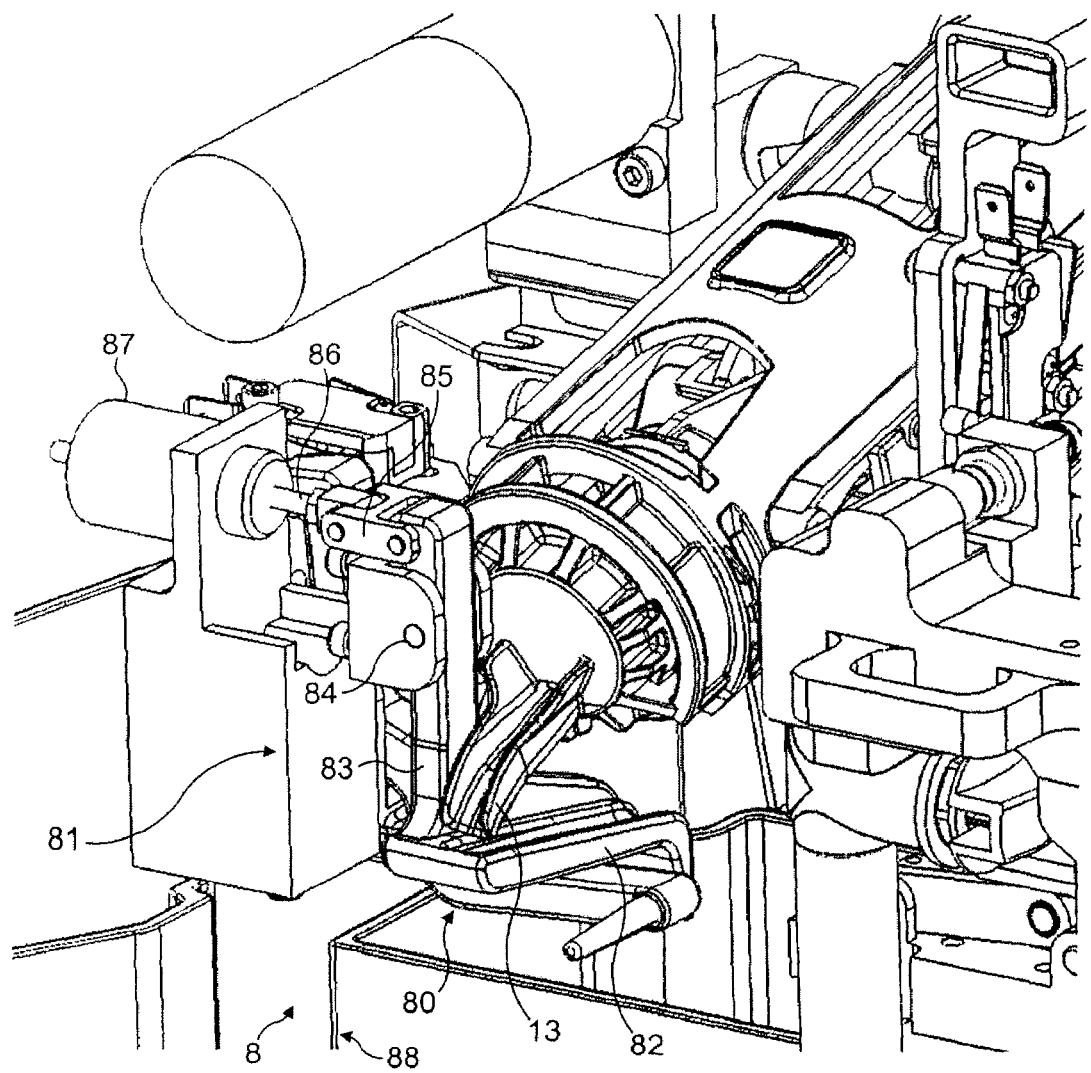
Figure 6:
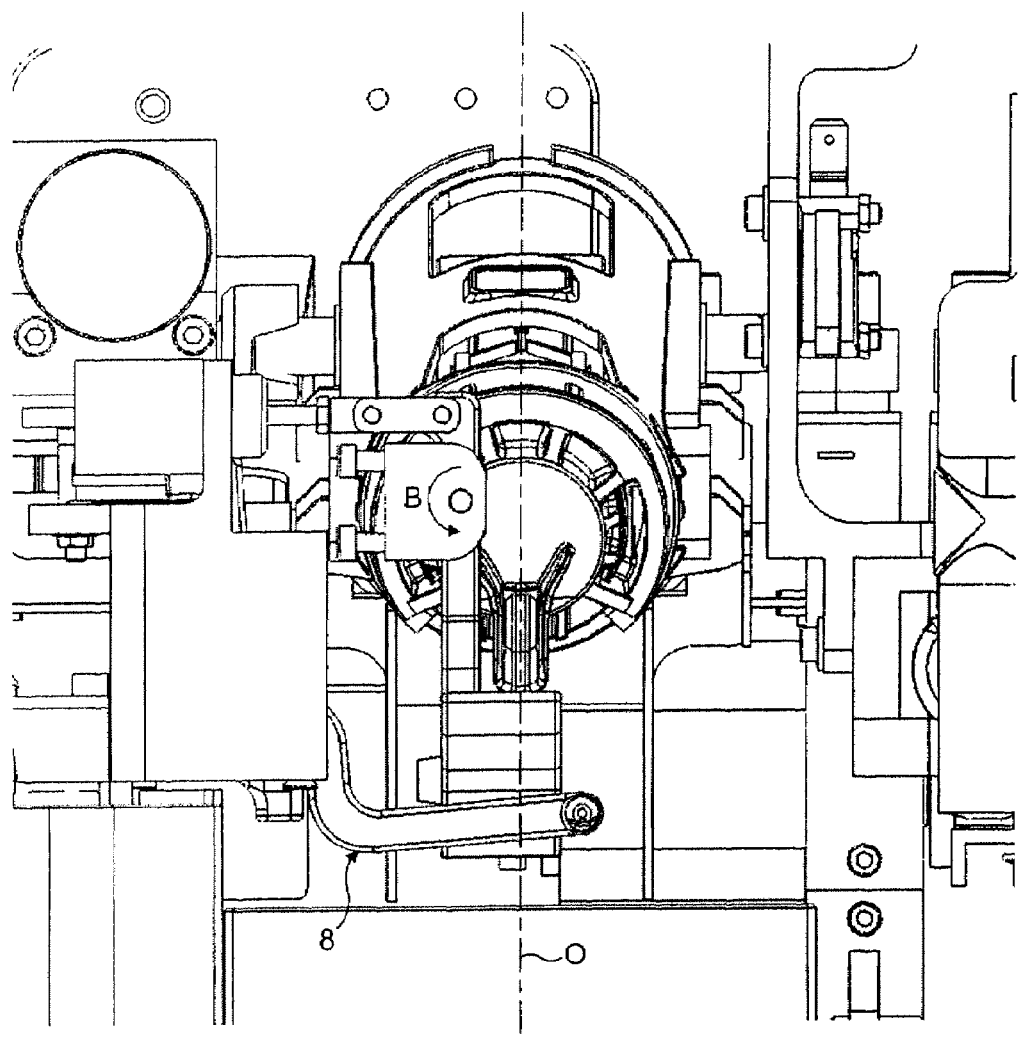

In the present example, the beverage outlet 13 is fixed and the drip collecting device 8 is movable to be selectively placed above the recipient that rests on the support plate and below the beverage outlet to collect liquid falling down from the beverage outlet as shown by FIGS. 5 and 6. More precisely, the drip-collecting device comprises a collecting device 80 which is movable between a collecting position (FIGS. 5 to 6) in which it is placed under the outlet and a retracted position (FIGS. 3 to 4) in which it is placed away relative to the vertical (Axis O in FIG. 4) of the outlet.

Therefore, the drip collecting device 80 is associated to an actuator 81 which is controlled by the control unit 61 (FIG. 7) to move it from the collecting position to the retracted position and vice versa. In the illustrated example, the drip-collecting device 80 has a L-shape with a portion of gutter 82 that extends upwardly by a base portion 83. The base portion is articulated via a crank mechanism comprising a fixed pivot joint 84 connected to the frame and a pivot joint 85 connected to a shaft 86 of a solenoid motor 87. As shown in FIG. 4, in a deployed position of the drive shaft, the base portion 83 is made to rotate along pivot joint 84 in direction A which results in the portion of gutter 82 to be withdrawn from the vertical axis O. In this position, the beverage can drip from the outlet to the recipient placed on the support plate. Conversely, as shown in FIG. 6, in a retracted position of the drive shaft, the base portion 83 is made to rotate in the opposite direction B (FIG. 6) which results in the portion of gutter 82 to be deployed at the vertical of axis O. In this position, the portion of gutter 82 is slightly inclined to deliver the collected liquid to a drip tray 88 positioned behind the vertical axis O. For this the portion of gutter ends at the vertical of the tank in the collecting position of the drip-collecting device so that all collected liquid is readily drained to the drip tray 88.

Figure 7:
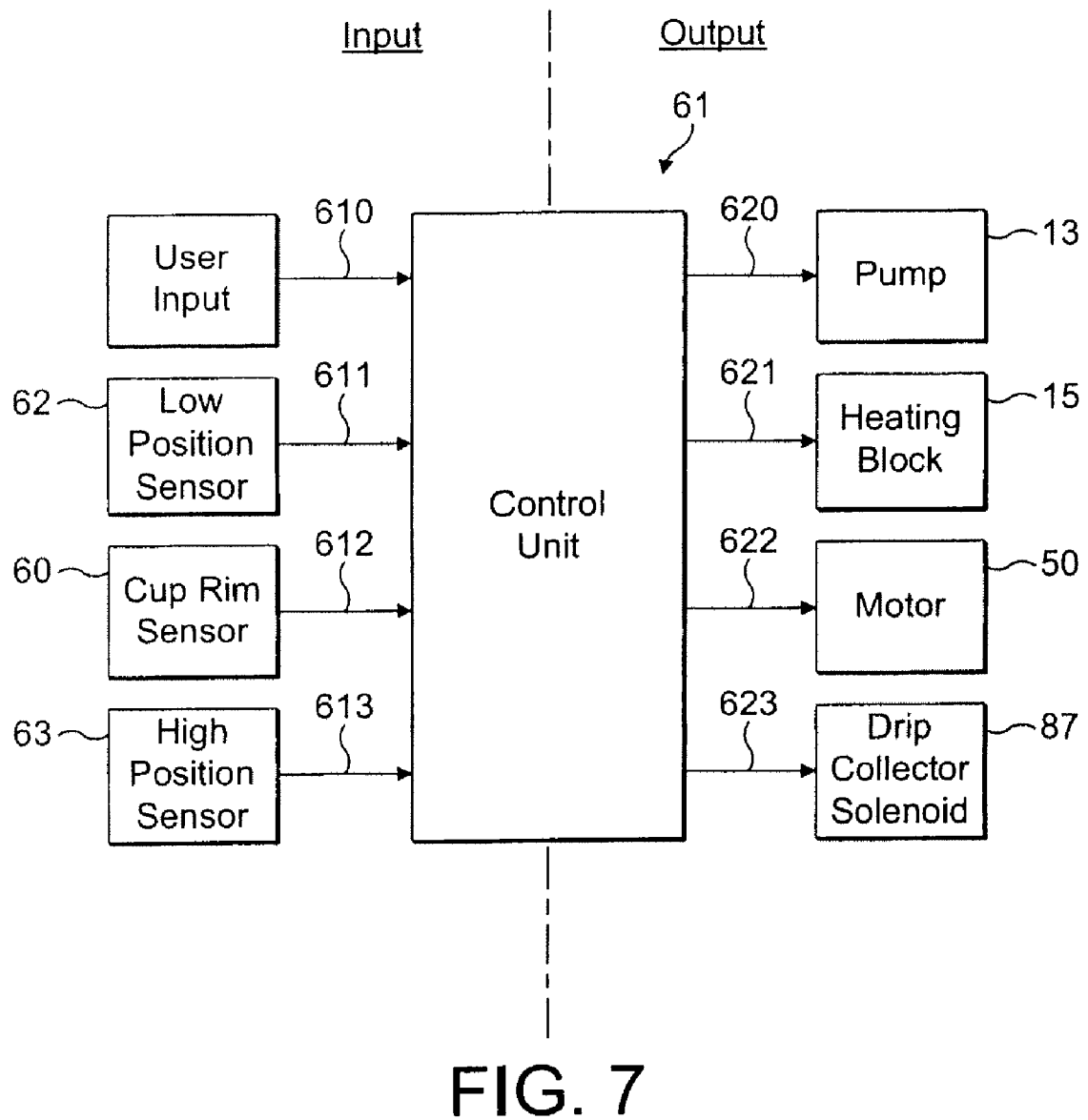
Figure 8:
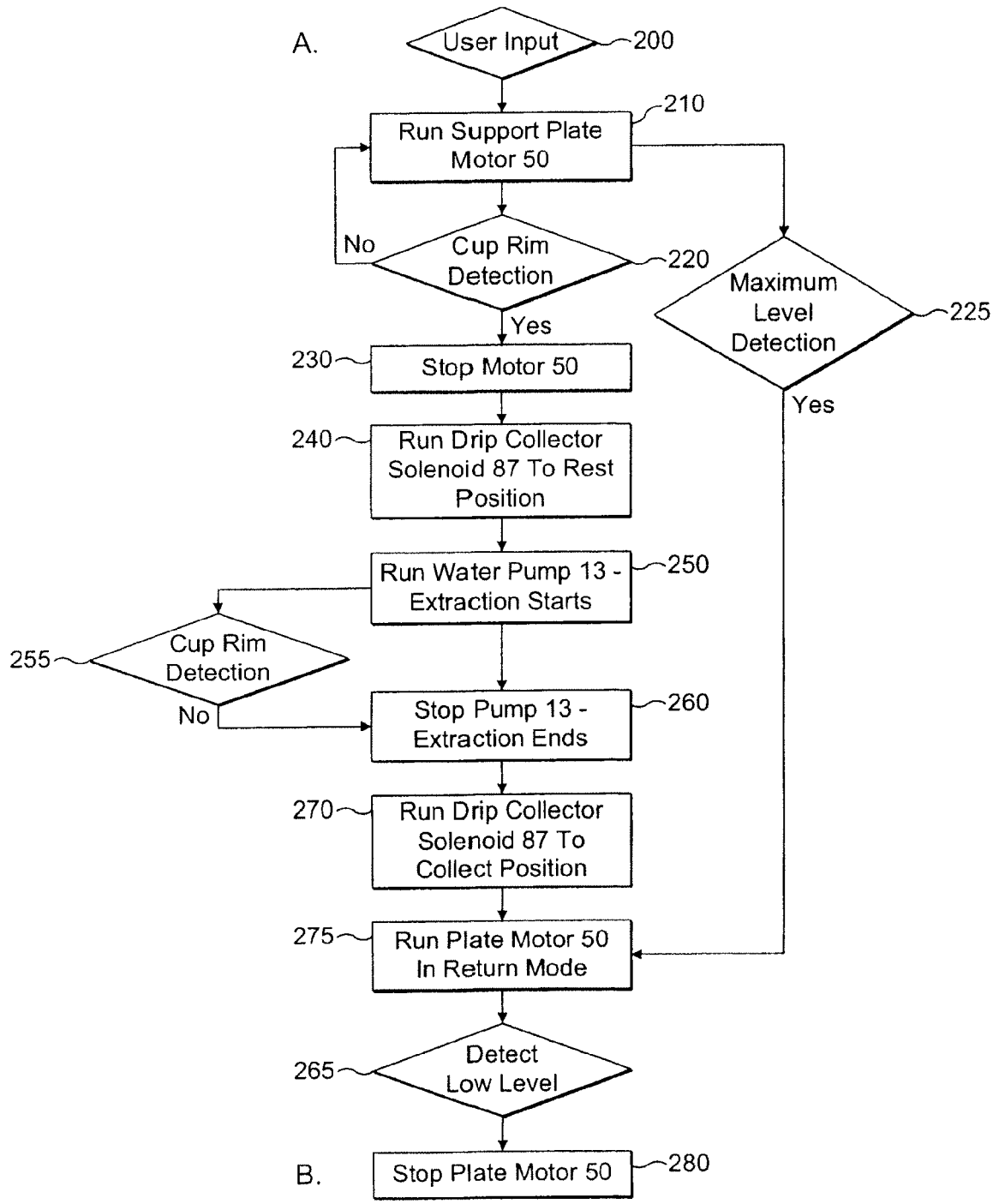
FIG. 8 shows an exemplary flow chart of the operations for preparing a beverage in the beverage machine of the invention.

An exemplary mode of operation for the beverage machine is depicted in FIGS. 7 and 8. FIG. 7 shows the control unit 61 receiving input signals 610, 611, 612, 613 from respectively, the user via a command button (not shown), the low position sensor 62, the cup rim detection sensor 60 and the high position sensor 63. The control unit sends output signals 620, 621, 622, 623 for respectively controlling the water pump 13, the heating block 15, the motor of the support plate displacement mechanism 50 and the drip collector solenoid 87. Other input and output signals can be added, as necessary, for other functions not described here.

As an example, the beverage operation cycle can be summarized in view of FIG. 8. Before the beverage cycle is activated by the user pressing on the selected command button in step 200, the support plate 4 is positioned in low position allowing a recipient to be placed in the central recess of the plate. The user input signal is received by the control unit that sends an output signal to start the support plate motor 50 in step 210. As a result, the support plate is moved upwards up to a point where the upper edge of the recipient is detected by the cup rim's sensor 60. As long as the recipient is not detected, the support plate continues to be moved upwards by the motor 50 until the maximal position is sensed by the high position sensor 63 in test 225. When the high position is detected, the control unit sends a signal to the DC motor 50 to be driven in reverse direction in step 275 which causes the support plate to return to its low position. When the low position level is detected in test 265, the motor 50 is stopped in step 280 and the cycle is over without beverage preparation having actually started.

When the rim detection test 220 becomes positive, i.e., a recipient has been detected by sensor 60, the motor 50 is stopped in step 230. The motor can be stopped immediately or after a time lag depending on the desired position of the recipient relative to the beverage outlet. After this step, the control unit sends a signal to the drip collector solenoid 87 to retract the collecting device 80 (step 240). In a next step 250, the extraction can start and the control unit starts the water pump 13. If during beverage delivery, the recipient went to be removed from the support plate as detected by test 255, the pump would be stopped in step 260. If the beverage delivery goes without this incident, the controller stops the pump after a predetermined time corresponding to the type of beverage to be delivered. In the next step 270, the drip collector solenoid 87 is moved back in the collect position. The motor 50 is reversed to return the support plate in low position at step 275 until the low position is detected resulting in the motor 50 to be stopped in step 280 and the cycle to be ended. Of course, this operational mode can vary in many ways.

Figure 9:
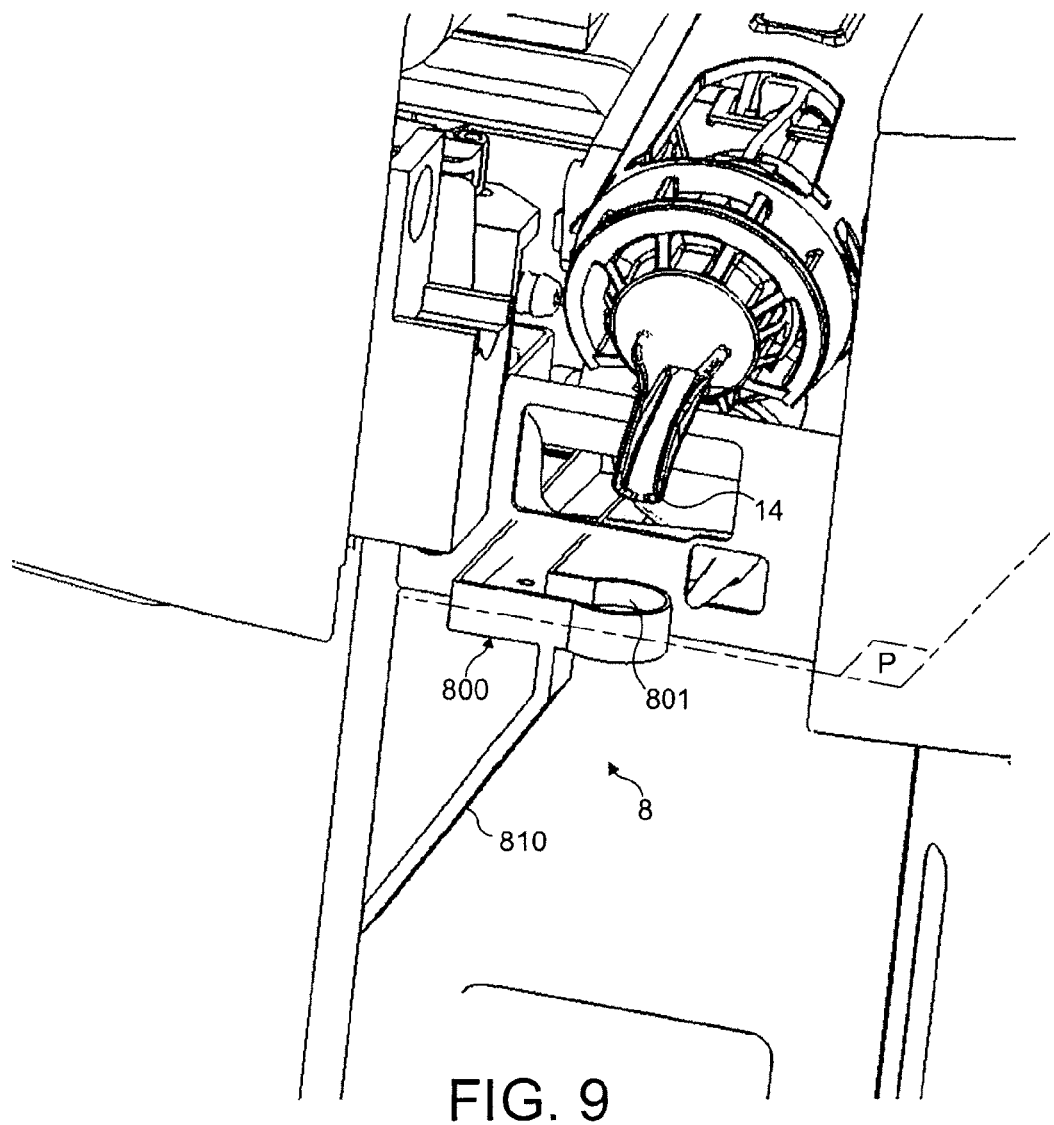
FIG. 9 shows a perspective view of a second embodiment of the drip collector system in collecting position.
Figure 10:
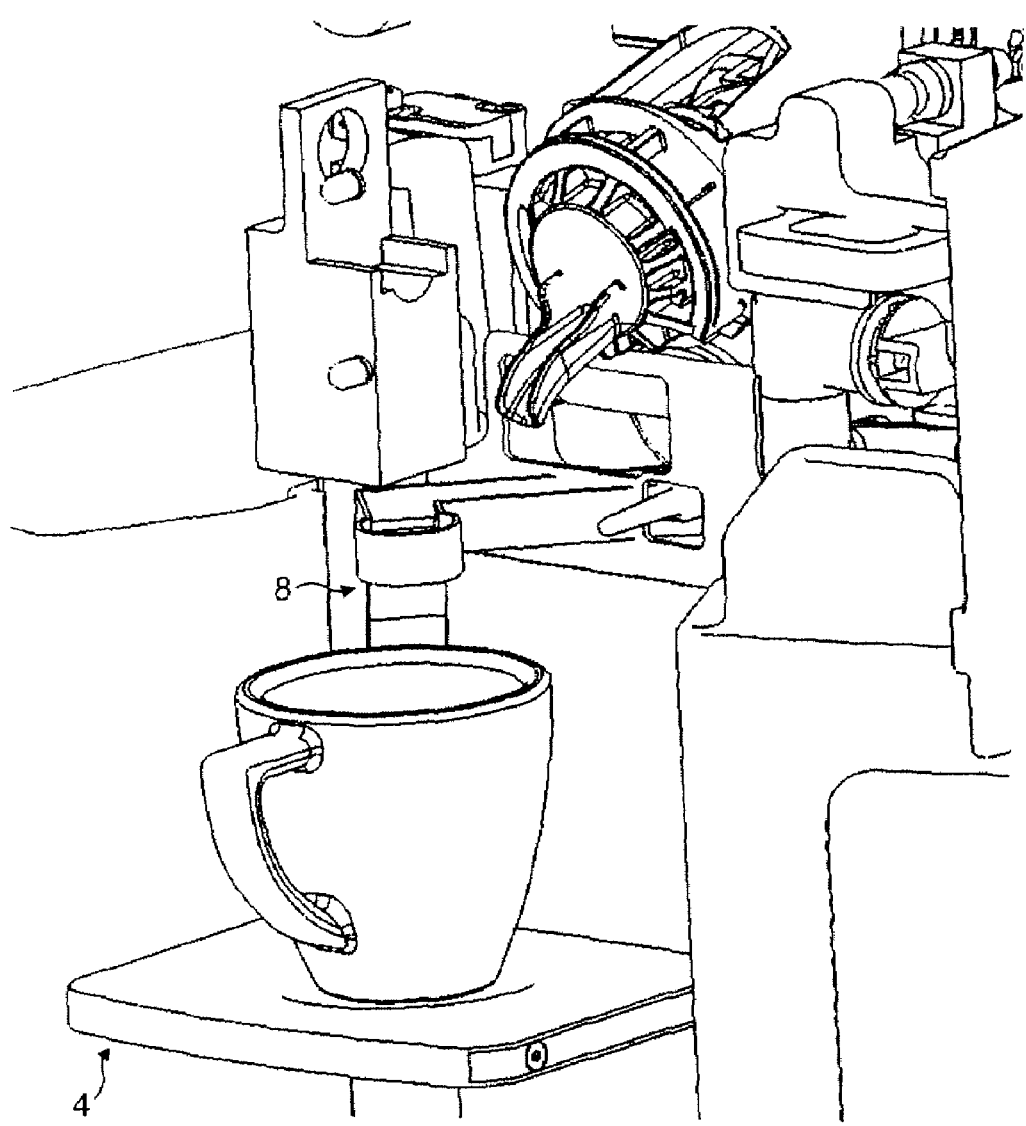
FIG. 10 shows a perspective view of the drip collector of FIG. 9 when engaged in retracted position by the recipient.

FIGS. 9 and 10 show a second embodiment of the drip-collecting device 8 of the invention. In this solution, the drip collector is moved from the deployed or collecting position to the retracted position by effect of the recipient mechanically engaging the device 8. For that, the drip collector 8 comprises a collecting device 800 with a gutter 801 adapted to collect the residual liquid dripping from the beverage outlet 14. The collecting device is mounted to the frame of the machine in a movable, controllable manner, e.g., in rotation along a vertical axis situated inside the machine such that it can move, from one position to the other and reciprocally, within a substantially vertical plane P. The collecting device 800 extends rearward by a mechanical actuating member, i.e., a lever 810 slanted outwardly in a manner to engage the side or upper edge of the recipient when the recipient is placed on the support plate or the support plate is elevated to the beverage delivery position. FIG. 10 illustrates the position when the collecting device 8 is pushed aside by the edge of the recipient as the support plate moves upwards, thus leaving the path of beverage free between the outlet 14 and recipient or cup.

Other possible solutions can be envisaged for the drip-collecting device such as a collecting device forming a chamber that covers the beverage outlet when the beverage delivery is not carried out. For example, the actuator can comprise an hydraulic system actuated to place the collecting device in a retracted position when water is supplied to the beverage preparation head and is actuated to place the collecting device in a collecting position when water is no longer supplied to the beverage preparation head.

What is claimed is:

1. A beverage machine for preparing a beverage comprising:
 a distance adjustment device that includes a movable support plate for adjusting a positionable recipient relative to at least one beverage outlet when resting on the support plate, wherein the support plate is movable relative to the at least one beverage outlet, and
 a displacement mechanism for displacing the support plate relative to the outlet, the displacement plate comprising:
  a motorized driver for driving the displacement mechanism, and
  a controller for controlling the actuation of the driver and which is configured to set a predetermined distance between the outlet and the recipient, with the controller further comprising at least one of:
   a low position sensor that senses a low position of the support plate corresponding to a load position for the recipient on the support plate and a control unit that commands the motorized driver to return the support plate to the low position and to stop the motorized driver in response to input received by the low position sensor; or
   a high position sensor that senses a maximal position of the support plate corresponding to a non-loaded position of the support plate and a control unit that commands the motorized driver to stop in the maximal position in response to input received by the high position sensor.

2. The beverage machine according to claim 1, wherein the a controller controls the distance as a function of a height related dimension of the recipient being placed on the support plate.

3. The beverage machine according to claim 2, wherein the controller comprises at least one sensor that detects the position of at least one part of the recipient being placed on the support plate and a control unit that stops the motorized driver in response to sensor input to the control unit.

4. The beverage machine according to claim 3, wherein the sensor is positioned in a predetermined position below the beverage outlet to detect the position of an upper edge of the recipient.

5. The beverage machine according to claim 1, wherein the motorized driver comprises:
 a drive electrical motor, and
 a continuous displacement transmission system that is arranged to be driven by the electrical motor to move the support plate in a continuous manner.

6. The beverage machine according to claim 5, wherein the continuous displacement transmission system comprises a gear rack attached to the support plate, and at least one gear wheel attached to the drive motor.

7. The beverage machine according to claim 5, wherein the continuous displacement transmission system comprises a threaded spindle attached to the drive motor and a complementary threaded ring attached to the support plate.

8. The beverage machine according to claim 1, wherein the controller comprises both the low and high position sensors.

9. The beverage machine according to claim 1, which further comprises a drip collecting device that is configured to collect liquid from the outlet, which drip collecting device is positionable to collect liquid between the beverage outlet and the recipient.

10. The beverage machine according to claim 9, wherein the drip collecting device comprises a collecting device which is movable between a collecting position beneath the beverage outlet, and a retracted position away from the outlet.

11. The beverage machine according to claim 10, wherein the drip collecting device is displaced from the collecting position to the retracted position by upward motion of the support plate.

12. The beverage machine according to claim 10, wherein the drip collecting device is associated with an actuator which is controlled by a control unit to move from the collecting position to the retracted position or from the retracted position to the collecting position.

13. The beverage machine according to claim 12, wherein the actuator comprises an electromagnetic solenoid or an electrical motor.

14. The beverage machine according to claim 1, further comprising a frame, a beverage outlet adapted to deliver a beverage into the recipient when placed in a beverage service area, and a drip collecting device which is configured to be selectively placed below or around the beverage outlet to collect liquid or froth when the beverage machine is not delivering the beverage or when the recipient is removed from the beverage service area.

15. The beverage machine according to claim 14, wherein the drip collecting device is configured to be selectively placed at a position above the recipient.

16. The beverage machine according to claim 14, wherein the drip collecting device is movable between a collecting position beneath the outlet and a retracted position away from the outlet.

17. The beverage machine according to claim 16, wherein the drip collecting device is displaced from the collecting position to the retracted position by upward motion of the support plate or by the recipient being placed on the support plate.

18. The beverage machine according to claim 17, wherein the drip collecting device comprises a collecting device and an arm or lever attached to the member that is engaged by the recipient to move the collector to the retracted position.

19. The beverage machine according to claim 16, wherein the drip collecting device is associated with an actuator which is controlled by a control unit to move from the collecting position to the retracted position or from the retracted position to the collecting position.

20. A method for collecting beverage drips from a beverage machine according to claim 9, which method comprises selectively placing the drip-collecting device in the service area to collect liquid falling from the beverage outlet before the liquid can reach the service area.

21. The method according to claim 20, which further comprises selectively placing the drip-collecting device in a collecting position in the service area when the machine is not delivering beverage or when the recipient is removed from the beverage service area.

22. A beverage machine for preparing a beverage comprising:
  a distance adjustment device that includes a movable support plate for adjusting a positionable recipient relative to at least one beverage outlet when resting on the support plate, wherein the support plate is movable relative to the at least one beverage outlet, and
  a displacement mechanism for displacing the support plate relative to the outlet, the displacement plate comprising:
    motorized drive means for driving the displacement mechanism; and
    control means for controlling the actuation of the drive means which is configured to set a predetermined distance between the outlet and the recipient, with the controller further comprising at least one of:
      (a) a low position sensor that senses a low position of the support plate corresponding to the recipient load position on the support plate and a control unit that commands the motorized drive means to return the support plate in low position and to stop the motorized drive means as a response of the input received by the low position sensor; or
      (b) a high position sensor that senses the maximal position of the support plate corresponding to a non-loaded position of the support plate and a control unit that commands the motorized drive means to stop the motorized drive means in this position as a response of the input received by the high position sensor; or
      (c) both (a) and (b).

23. The beverage machine according to claim 22, wherein the control means comprises both the low and high position sensors.

* * * * *